United States Patent [19]

Kilner et al.

[11] Patent Number: 4,587,350

[45] Date of Patent: * May 6, 1986

[54] PROCESS FOR THE PRODUCTION OF TRIMELLITIC ANHYDRIDE

[75] Inventors: Peter H. Kilner, Sunnyvale, Calif.; Joseph P. Egan, Jr., Plainfield, Ill.; Stephen G. Ceisel, Shorewood, Ill.; Wayne P. Schammel, Naperville, Ill.

[73] Assignee: Amoco Corporation, Chicago, Ill.

[*] Notice: The portion of the term of this patent subsequent to Aug. 27, 2002 has been disclaimed.

[21] Appl. No.: 744,925

[22] Filed: Jun. 14, 1985

Related U.S. Application Data

[63] Continuation-in-part of Ser. No. 591,468, Mar. 20, 1984, Pat. No. 4,537,978.

[51] Int. Cl.$^4$ ............................................ C07D 307/89
[52] U.S. Cl. .................................................... 549/245
[58] Field of Search ........................................ 549/245

[56] References Cited

U.S. PATENT DOCUMENTS 3,732,257  5/1973  Knobloch et al. ................... 549/245
3,853,924  12/1974  Meyer et al. ........................ 549/245

*Primary Examiner*—Richard L. Raymond
*Attorney, Agent, or Firm*—Gunar J. Blumberg; William T. McClain; William H. Magidson

[57] ABSTRACT

A process for the oxidation of pseudocumene to trimellitic acid anhydride is disclosed which comprises catalytic oxidation of pseudocumene with air in the presence of acetic acid in an oxidation zone in the liquid phase wherein the weight ratio of acetic acid to pseudocumene is in the range of about 0.5–4.0:1.0 and the catalyst comprises one or more heavy metal oxidation catalysts comprising zirconium, cobalt, and manganese to provide about 0.1 to about 0.4 weight percent total metals based on pseudocumene and a source of bromine. The addition of the bromine component is controlled to provide a total of about 0.10 to about 0.30 weight percent total bromine based on pseudocumene. The total weight ratio of bromine ions to total metals ions is about 0.5 to about 2.0. The zirconium content is about 1 to about 5% and the manganese content is about 14 to about 60% each by weight of the total metals. The reaction temperature is about 100° C. to about 250° C. The acetic acid and water of reaction are withdrawn during the last 5 to about 20% of the reaction.

4 Claims, No Drawings

PROCESS FOR THE PRODUCTION OF TRIMELLITIC ANHYDRIDE

BACKGROUND

This is a continuation-in-part application of Ser. No. 591,468 filed on Mar. 20, 1984, now U.S. Pat. No. 4,537,978.

The field of this invention relates to the liquid-phase oxidation of pseudocumene and to the withdrawing of acetic acid solvent and water of reaction during the last 5 to 20% time period of the reaction, thus increasing the final reaction solids content by about 5 to about 20% during crystallization. This invention also relates to the recycling of filtrate to the crystallization section to maintain a pumpable slurry, thus obtaining a higher yield of trimellitic anhydride from pseudocumene.

The possibility of using liquid-phase instead of vapor-phase oxidation for the preparation of benzene carboxylic acids was first indicated by the disclosure in U.S. Pat. No. 2,245,528 of the catalysis provided by transition or variable-valence metals, especially cobalt, in a liquid phase of saturated lower aliphatic acid at temperatures from 100° to 320° C. and pressures to maintain the liquid phase of the aliphatic acid. Such catalysis, according to said patent, was advantageously promoted by the use of a ketone, such as methylethyl ketone, or an aldehyde, such as acetaldehyde. Unfortunately, such aldehyde- or ketone-promoted variable-valence metal catalysis was useful only for converting mono-, di-, or trimethylbenzenes to their respective benzene monocarboxylic acids: benzoic, toluic, and dimethyl benzoic acids. Two separate, later, and somewhat parallel lower temperature (80°–100° C.) modifications of the aldehyde- or ketone-promoted cobalt catalysis in a liquid phase of acetic acid did provide commercially feasible conversion of xylenes to phthalic acids, especially p-xylene to terephthalic acid, but only at the expense of using rather high concentrations of cobalt with respect to p-xylene.

The disadvantages of using high concentrations of cobalt promoted with large quantities of aldehyde or ketone were overcome and, at the same time, a greater choice of variable-valence metal oxidation catalysts was made available and a wider choice of alkyl-substituted benzene starting materials for benzene di-, tri-, and higher carboxylic acids was provided by the discovery of the unique promotional effect on said variable-valence metal by bromine ion, provided per se or formed in situ with or without acidic reaction medium provided by $C_1$–$C_8$ monocarboxylic acids having no hydrogens on a tertiary carbon, such as benzoic acid and the saturated aliphatic monocarboxylic acids, preferably acetic acid. Such bromine-variable-valence metal catalysis was first disclosed in U.S. Pat. No. 2,833,816.

The bromine-polyvalent metal catalysis in acetic acid solvent has been in commercial use in many countries for the manufacture of terephthalic acid from p-xylene for many years. However, in the absence of acetic acid solvent, the best yield of a single phthalic acid (e.g., terephthalic acid) on a once-through basis of the xylene amounted to about 20 weight (12.8 mole) percent according to U.S. Pat. No. 2,833,816. According to U.S. Pat. No. 3,920,735, the Mn-Br and Co-Mn-Br catalyst system is improved by the addition of zirconium. However, not mentioned, but illustrated in Tables I, II, and IV in U.S. Pat. No. 3,920,735 is the fact that when part of the zirconium is added, combustion of the feedstock to carbon dioxide increases.

A novel mode of conduct for a better oxidation of pseudocumene to produce trimellitic anhydride has been discovered. This improved mode of conduct provides a higher yield which results from the withdrawal of condensed solvent during the last 5 to 20% of the period of the pseudocumene oxidation. This improved process comprising the withdrawal of solvent and water of reaction during the last 5 to about 20% of the reaction time allows us to increase the crystallizer effluent up to 70–75% solids instead of the 50–60% solids without our novel solvent draw-off process. The recovery of trimellitic acid by the filter increased from about 92.2% to about 97.0% by the use of our novel process.

In the batchwise oxidation of pseudocumene the exothermic heat of reaction vaporizes some of the liquid solvent which is carried out of the reactor by the process air. The solvent is condensed and returned to the reactor as reflux. This liquid reflux is reheated toward the end of the reaction cycle to ensure temperatures high enough to bring the oxidation to completion. After reaction, the reactor contents are depressurized and trimellitic acid is crystallized out to form a 50–60% solids slurry (close to the maximum solids concentration that is pumpable). The solids are filtered out and further processed into final product. The filtrate is disposed of and therefore represents a significant yield loss.

Under the conditions embodied by our novel process the solvent condensed out of the reactor vent gas is withdrawn and not returned as reflux to the reactor. Solvent withdrawal maintains reactor temperatures high enough to complete the reaction thereby saving energy due to the elimination of reflux reheating. The withdrawn solvent is rich in water as opposed to acetic acid. Therefore, since trimellitic acid is ten times more soluble in water than in acetic acid, with water rich solvent withdrawal the crystallizer effluent can be thickened to 70% solids instead of 60%, thereby recovering more trimellitic acid and reducing filtrate losses. In practice, a slurry containing more than 70% solids is difficult to pump. To ease operating problems, enough filtrate, which is saturated with trimellitic acid, is pumped to the crystallization section to provide pumpability while maintaining an overall increase in yield. Usually, about 20 to about 80% of the total filtrate is pumped to the crystallization section.

The present inventive oxidation of pseudocumene comprising the withdrawal of the condensed solvent (acetic acid) and water of reaction during the last 5 to about 20% of the oxidation reaction period is conducted using acetic acid reaction medium in the weight ratio to pseudocumene (PSC) of about 0.5:1.0 to about 4.0:1.0. The metal oxidation catalyst components are cobalt, zirconium, and manganese or cobalt and manganese. Total metal concentration based on PSC is in the range of about 0.1 to about 0.4, preferably about 0.22 to about 0.32, weight percent in combination with a source of bromine providing a bromine-to-total metal ratio of about 0.5 to about 2.0, preferably about 0.7 to about 1.7, on a weight basis. The manganese component of the catalyst is in the range of about 14.0 to about 60.0 weight percent based on the total weight of catalyst metals. The zirconium content of the total metals used is in the range of about 1.0 to about 5.0, preferably about 2.0 to about 4.0, weight percent of total metals. The cobalt component of the catalyst is in the range of about 35 to about 80 weight percent of the total metals.

The oxidation of PSC is conducted batchwise. All of the PSC and most (90–99%) of the acetic acid and initial amount of catalyst components are charged at or near oxidation initiation temperature, preferably at about 100° C. to about 165° C., and at a pressure to maintain liquid-phase conditions. Then, pressurized air is injected into the reaction mixture and the reaction temperature is permitted to increase by heat evolved by the oxidation reaction to about 175° C. to about 250° C.

The total bromine added can be from a single source of bromine, for example, ionic bromine sources (HBr, NaBr, NH₄Br, and the like) or from a combined form of bromine, for example, organic bromines such as benzyl bromine, tetrabromoethane, and others.

Our novel process relates to the liquid-phase oxidation of pseudocumene to trimellitic anhydride using cobalt, manganese, and/or other variable-valence metals, such as zirconium plus bromine. A useful catalyst for our process is a zirconium-cobalt-manganese-bromine catalyst wherein the molecular ratio of zirconium to cobalt is about 1 to about 10 to about 1 to about 50 and the oxidation is conducted at a temperature in the range of about 100° C. to about 250° C., which process comprises conducting a batch oxidation of the pseudocumene so that the concentration of bromine in the first stage is 0 to about 0.5 mole per mole of metals while all the remaining bromine is added during the second stage. The total amount of bromine added is about 50 to about 200 weight percent of the total metal catalysts present, the reaction is completed in a noncontinuous process at a temperature of about 140° C. to about 250° C., and the solvent and water of reaction is withdrawn during the last 5 to about 20% of the period of the reaction, usually during the last 5 to 20 minutes of the reaction, leaving a solids content in the crystallizer effluent of about 70 to about 75 weight percent.

In the preferred embodiment of our process for the oxidation of pseudocumene with molecular oxygen to trimellitic anhydride under liquid-phase conditions in the presence of a zirconium-cobalt-manganese-bromine catalyst, the molecular ratio of zirconium to cobalt is about 1:10 to about 1:40 and the temperature is in the range of about 100° C. to about 250° C. This process comprises conducting a batch oxidation of the pseudocumene so that in the first stage no bromine is added or the amount of bromine added is below 30 weight percent of the total bromine to be added. The reaction is completed in a non-continuous process at a temperature of about 140° C. to about 250° C. and during the last 5 to about 20 percent of the reaction time. The solvent and water of reaction are withdrawn leaving about 70 to about 75 weight percent solids in the crystallizer effluent.

Our novel process relates to the liquid-phase oxidation of pseudocumene to trimellitic anhydride using cobalt, manganese, and/or other variable-valence metals, such as zirconium plus bromine. A useful catalyst for our process is a zirconium-cobalt-manganese-bromine catalyst wherein the molecular ratio of zirconium to cobalt is about 1 to about 10 to about 1 to about 50 and the oxidation is conducted at a temperature in the range of about 100° C. to about 250° C., which process comprises conducting a batch oxidation of the pseudocumene so that the concentration of bromine in the first stage is 0 to about 0.5 mole per mole of metals while all the remaining bromine is added during the second stage. The total amount of bromine added is about 50 to about 200 weight percent of the total metal catalysts present, the reaction is completed in a batch process at a first stage temperature of about 100° C. to about 165° C. and a second stage temperature of about 150° C. to about 250° C., and the solvent and water of reaction is withdrawn during the last 5 to about 20% of the period of the reaction, usually during the last 5 to about 20 minutes of the reaction, leaving a solids content in the crystallizer effluent of about 60 to about 70 weight percent.

Our novel process also relates to the liquid-phase oxidation of aromatic hydrocarbons having two or more alkyl groups attached to the aromatic ring using cobalt, manganese, and/or other variable-valence metals, such as zirconium plus bromine. Our novel invention is a process for the oxidation of di- or trimethylbenzenes with molecular oxygen to benzene di- or tricarboxylic acid under liquid-phase conditions in the presence of a zirconium-cobalt-manganese-bromine catalyst wherein the molecular ratio of zirconium to cobalt is about 1 to about 10 to about 1 to about 50 at a temperature in the range of about 100° C. to about 250° C. Our novel process also comprises conducting a semicontinuous oxidation of the pseudocumene so that the concentration of the polycarboxylic acids is very low permitting only partial oxidation of the pseudocumene moiety, thus avoiding the poisoning of the catalyst and completing the reaction in a noncontinuous process at a temperature of about 140° C. to about 175° C. to about 150° C. to about 250° C.

As an aid in verifying our invention we have used several computer simulations of the TMLA process to evaluate the effects of solvent withdrawal. The effect of solvent drawoff on final reactor conditions is shown in the results below of computer simulations of reactor operations.

| Case | Final Reactor Temp °F. | Final Liquid Composition, Wt. % | | | % Reduction in Weight |
|---|---|---|---|---|---|
| | | Acetic Acid | Water | TMLA | |
| No solvent withdrawal-reflux reheated | 396 | 43.0 | 18.0 | 39.0 | — |
| Solvent withdrawal during last 7 minutes of reaction-no reflux reheating | 401 | 42.2 | 15.1 | 42.7 | 8.6 |

The above results show that solvent withdrawal will maintain reactor temperatures high enough to complete the reaction thereby eliminating reflux reheating and reducing energy costs. The withdrawal of water-rich solvent reduces the water content of the reactor effluent from 18.0 to 15.1 weight percent. Since TMLA is 10 times more soluble in water than in acetic acid, the removal of water-rich solvent would enhance recovery of TMLA in the crystallization and filter operations.

The results of a computer simulation of the crystallizer operations are shown below:

| | No Solvent Withdrawal | Solvent Withdrawal |
|---|---|---|
| Crystallizer Feed Temp., °F. | 357 | 362 |
| Crystallizer Feed Pressure, psia | 120 | 120 |

-continued

|  | No Solvent Withdrawal | Solvent Withdrawal |
|---|---|---|
| Feed Composition, wt % | | |
| Acetic Acid | 43.6 | 41.2 |
| Water | 14.7 | 11.6 |
| TMLA | 41.7 | 47.2 |
| Crystallizer Effluent Temp., °F. | 119 | 128 |
| Crystallizer Effluent Pressure, psia | 1.0 | 1.0 |
| Crystallizer Effluent Composition, wt % | | |
| Acetic Acid | 33.1 | 26.0 |
| Water | 6.5 | 3.8 |
| TMLA | 60.4 | 70.2 |

The data show that with solvent withdrawal the TMLA content of the crystallizer effluent can be increased from 60.4 to 70.2 weight percent. Recycling of saturated filtrate is necessary in practice to dilute a 70-weight percent TMLA stream to a 60-weight percent TMLA stream to maintain pumpability.

The following examples illustrate the preferred embodiment of this invention. It will be understood that the examples are for illustrative purposes only and do not purport to be wholly definitive with respect to the conditions and scope of the invention.

EXAMPLE 1

To experimentally determine the feasibility of solvent withdrawal, a series of runs were performed and these cases are listed in Table I. Solvent withdrawal is performed by running standard batch oxidations until about 10 minutes remain in the run. At this point, all of the condensate is diverted out of the reactor. Typically, 30–40% of the total solvent is removed during this period of time. Analysis of the condensate indicates that it is 33% $H_2O$ and 67% acetic acid.

Table I has the results of two solvent withdrawal runs together with the results of two base case batch runs. Despite small differences in pressure and temperature profiles during these runs, the product distribution for each of the four runs is essentially identical. Therefore, these experiments show that solvent withdrawal would not adversely affect product quality or reactor yield. Because there is no influence on the yield of TMLA from the reactor and because the yield losses in the solvent will be much less, it is clear that the overall yield of TMLA will increase substantially as a result of this invention.

TABLE I

THE EFFECT OF LATE SOLVENT WITHDRAWAL ON TMLA YIELD AND QUALITY

|  | Base Case | Base Case Low Late Temperature[1] | Solvent Drawoff High Pressure Case[2] | Solvent Drawoff Low Pressure Case[3] |
|---|---|---|---|---|
| Run No. | 8336-002 | 8046-180 | 8046-184 | 8046-188 |
| Wt % Dimethyl Benzoic Acids | 0.08 | 0.10 | 0.09 | 0.09 |
| Wt % Methyl | 0.26 | 0.37 | 0.32 | 0.33 |
| Dibasic Acids | | | | |
| Wt % OA | 0.70 | 0.72 | 0.74 | 0.73 |
| Wt % TA | 0.43 | 0.38 | 0.39 | 0.39 |
| Wt % IA | 0.53 | 0.51 | 0.57 | 0.50 |
| Wt % High Boilers | 2.55 | 2.58 | 2.77 | 2.32 |
| $CO_x$, Mole % of PSC | 6.5 | 5.6 | 6.8 | 6.0 |
| Run Time, Min. | 73 | 71 | 74 | 76 |

[1] W/O reflux heat-low temperature case (final temperature = 385° F.).
[2] Final temperature = 417° F., final pressure = 350 psig, 34% of total solvent removed in last 12 minutes.
[3] Final temperature = 410° F., final pressure = 320 psig, 36% of total solvent removed in last 14 minutes.

We claim:
1. A process for oxidizing pseudocumene to trimellitic anhydride which comprises catalytic oxidation of pseudocumene with air in the presence of acetic acid in an oxidation zone wherein liquid-phase conditions are maintained and wherein the weight ratio of acetic acid to pseudocumene is in the range of about 0.5–4.0:1.0 and the catalyst comprises one or more heavy metal oxidation catalysts comprising zirconium, cobalt, and manganese to provide about 0.1 to about 0.4 weight percent total metals based on pseudocumene and a source of bromine and to provide a total of about 0.10 to about 0.30 weight percent total bromine based on pseudocumene, wherein the total weight ratio of bromine ions to total metals ions is about 0.5 to about 2.0, the zirconium content is about 1 to about 5%, and the manganese content is about 14 to about 60%, each metal by weight of the total metals and wherein the cobalt content is about 35 to about 80 weight percent, the temperature in the last stage is upward from about 175° C. to about 250° C., the temperature in the preceding stage is between about 100° C. and about 165° C., and wherein acetic acid solvent and water of reaction are withdrawn during the last 5 to about 20% of the oxidation reaction.

2. The process of claim 1 wherein the acetic acid solvent and water of reaction are withdrawn during the last 5 to about 10 minutes of the reaction.

3. A process for the oxidation of pseudocumene with molecular oxygen to trimellitic acid under liquid-phase conditions in the presence of a zirconium-cobalt-manganese-bromine catalyst wherein the molecular ratio of zirconium to cobalt is about 1:10 to about 1:50 at a temperature in the range of about 100° C. to about 250° C., which process comprises conducting a semicontinuous oxidation of the pseudocumene so that only one methyl moiety on the average on the benzene ring is converted to the carboxylic acid group, thus avoiding the poisoning of the catalyst and completing the reaction in a noncontinuous process at a temperature of about 140° C. to about 175° C. to about 150° C. to about 250° C., and wherein acetic acid and water of reaction are withdrawn during the last 5 to about 20% of the oxidation reaction.

4. The process of claim 3 wherein about 10 to about 20% of the filtrate saturated with trimellitic acid is pumped back to the crystallizer section to provide pumpability of the trimellitic acid slurry while maintaining a recovery of trimellitic acid by the filter over 90 mole percent.

* * * * *